(12) United States Patent
Lizzi et al.

(10) Patent No.: US 6,488,626 B1
(45) Date of Patent: Dec. 3, 2002

(54) ULTRASONIC SENSING BY INDUCED TISSUE MOTION

(75) Inventors: Frederic L. Lizzi, Tenafly, NJ (US); Sheikh Kaisar Alam, Somerset, NJ (US)

(73) Assignee: Riverside Research Institute, New York, NY (US)

( * ) Notice: Subject to any disclaimer, the term of this patent is extended or adjusted under 35 U.S.C. 154(b) by 0 days.

(21) Appl. No.: 09/543,507

(22) Filed: Apr. 6, 2000

Related U.S. Application Data

(60) Provisional application No. 60/128,148, filed on Apr. 7, 1999.

(51) Int. Cl.[7] ............... A61B 6/00; A61B 8/00; A61B 8/12; A61B 8/14
(52) U.S. Cl. ............... 600/437; 600/439; 600/459; 601/2; 601/3; 601/4
(58) Field of Search ............... 601/2, 3, 4; 600/459, 600/439

(56) References Cited

U.S. PATENT DOCUMENTS

| | | | | |
|---|---|---|---|---|
| 5,558,092 A | * | 9/1996 | Unger et al. | |
| 5,657,760 A | * | 8/1997 | Ying et al. | |
| 5,697,897 A | * | 12/1997 | Buchholtz et al. | |
| 5,882,302 A | * | 3/1999 | Driscoll, Jr. et al. | |

OTHER PUBLICATIONS

Nightingale, Kathryn, et al The Use of Radiation Force Induced Tissue Displacements to Image Stiffness: A Feasibility Study, 23rd International Symposium on Ultrasonic Imaging and Tissue Characterization, May 27–29, 1998.

* cited by examiner

*Primary Examiner*—Marvin M. Lateef
*Assistant Examiner*—Jeoyuh Lin
(74) *Attorney, Agent, or Firm*—Baker Botts LLP

(57) ABSTRACT

Radiation pulses from a high energy therapeutic ultrasound system are used to stimulate tissue motion by radiation pressure. The tissue motion is monitored using a diagnostic ultrasound system.

23 Claims, 4 Drawing Sheets

ULTRASONIC SENSING BY INDUCED TISSUE MOTION

This application is based on and claims the benefit of Provisional Application Ser. No. 60/128,148 filed Apr. 7, 1999.

BACKGROUND OF THE INVENTION

This invention relates to ultrasonic characterization of tissue and particularly to characterization of the mechanical properties of tissue during treatment thereof with therapeutic ultrasound. In a paper entitled "Sonoelasticity Images Derived from Ultrasound Signals in Mechanically Vibrated Tissues," by R. M. Lerner, S. R. Huang and K. J. Parker published in *Ultrasound Medical Biology,* vol. 16, pp. 231–239, 1990 there is described a technique for measuring the mechanical properties of tissue by inducing mechanical vibrations therein and measuring ultrasonic echos from within the tissues during vibration thereof. Such procedures can sense the effective stiffness of tissue constituents and produce cross-sectional images depicting induced displacement or strain.

In U.S. Pat. No. 4,484,569, which is assigned to the assignee of the present invention, there is described a combined transducer for providing diagnostic imaging using ultrasound, and for providing therapeutic application of high intensity focused ultrasound for treatment of tissue by producing lesions therein.

In a paper entitled "Elastography Imaging of Thermal Lesions in Soft Tissue: A Preliminary Study In Vitro" in *Ultrasound Medical Biology,* vol. 24, pp. 1449–1458 (1998) Stafford et al. have shown that internal thermal lesions induced by high intensity focused ultrasound could perturb the elastic moduli of normal tissue and produce ultrasonically detectable changes in displacement, measured after the treated tissue was imbedded in a gel block. These studies used a large paddle to mechanically induce external displacement of the tissue.

It is an object of the present invention to provide a new and improved method for measuring the mechanical properties of tissue using ultrasound, and in particular a method for providing measurement of induced lesions in tissue during therapeutic application of high intensity focused ultrasound thereto.

SUMMARY OF THE INVENTION

In accordance with the invention there is provided a method for evaluating tissue characteristics, which includes operating an ultrasonic therapeutic transducer to insonify a region of tissue and cause induced tissue displacement. An ultrasonic diagnostic transducer is operated to observe the tissue displacement and thereby evaluate the mechanical characteristics of the tissue.

According to a preferred method the therapeutic transducer insonifies the tissue along a radiation axis and the diagnostic transducer transmits and receives ultrasonic signals along the same radiation axis. Preferably the ultrasonic therapeutic transducer is operated during a first selected time interval and the ultrasonic diagnostic transducer is operated during a second selected time interval immediately following the first selected time interval.

According to the invention there is provided a method for ultrasonic treatment of tissue including locating a tissue region to be treated using diagnostic ultrasound, radiating the tissue region using high power therapeutic ultrasound radiation and observing mechanical characteristics in the tissue region using the diagnostic ultrasound to evaluate effectiveness of the therapeutic ultrasound radiation.

In a preferred method of treatment, locating the tissue region is done by observing baseline mechanical characteristics of the tissue region. In addition there may be provided a reduced energy stimulus pulse of the therapeutic ultrasound radiation to irradiate the tissue during a first selected time interval. Mechanical characteristics of the tissue are observed during a second selected time interval immediately following the first time interval using diagnostic ultrasound thereby to observe baseline characteristics of the tissue region. After ultrasonic treatment of the tissue the tissue characteristics can be observed by irradiating the tissue with a reduced energy stimulus pulse of the therapeutic ultrasound radiation and thereafter observing mechanical characteristics of the tissue region using diagnostic ultrasound. In practicing the treatment method of the invention the location of the focal volume of the therapeutic ultrasound radiation within tissue may be determined. A reduced energy pulse of therapeutic ultrasound radiation may be supplied to the tissue during a first selected time interval and the mechanical response of the tissue region to be treated will be observed during a second selected time interval immediately following the first selected time interval using the diagnostic ultrasound to thereby locate the focal volume of the therapeutic radiation in the tissue.

For a better understanding of the present invention, together with other and further objects, reference is made to the following description, taken in conjunction with the accompanying drawings, and its scope will be pointed out in the appended claims.

DESCRIPTION OF THE PREFERRED EMBODIMENT

Figure 1:
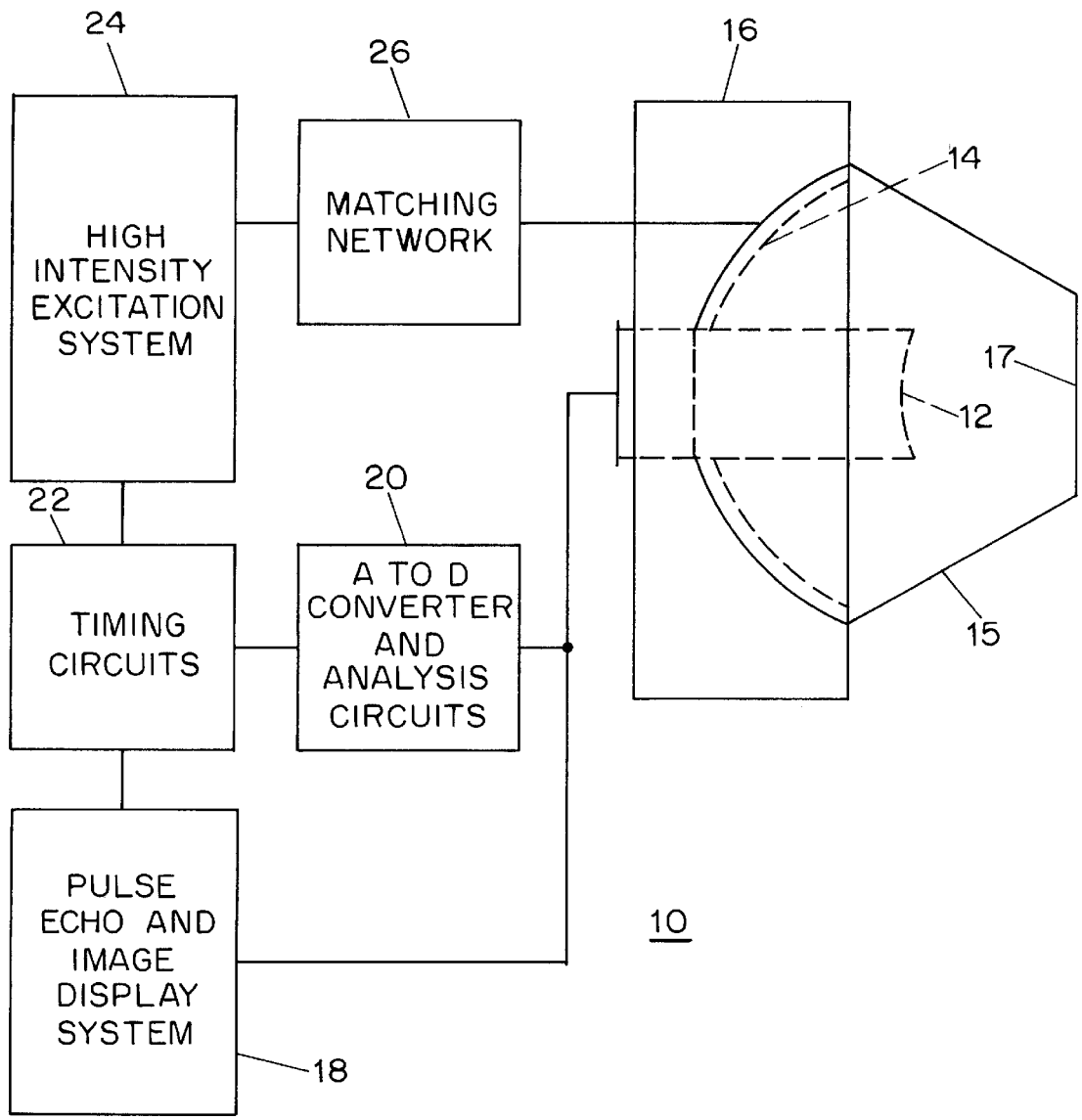
FIG. 1 is a block diagram of a therapeutic and diagnostic ultrasound system useful in connection with the practice of the method of the present invention.

Referring to FIG. 1 there is shown an ultrasonic imaging and therapeutic system arranged to carry out the method of the present invention. The system includes a transducer assembly 16 having a high intensity focused ultrasound therapeutic transducer 14 in the form of a spherical shell segment for radiating high intensity ultrasound toward a focal region. Transducer 14 is typically made of a piezoelectric ceramic shell which is coated with conductive coating on both surfaces. Transducer 14 may have a diameter of 80 mm and a focal length defined by its radius of curvature of 90 mm. A diagnostic transducer 12 having a diameter of 24 mm is inserted through an opening in the center of therapeutic transducer 14 and has a radiating aperture which provides a focused therapeutic radiation beam which has a focal region at or near the focal region of therapeutic transducer 14. Alignment can be achieved by using the high intensity beam to form a "lesion" on the surface of a wax block, which can be sensed by the diagnostic transducer to provide proper mechanical adjustment. This transducer assembly includes a conical housing 15 which may be filled with degassed water to conduct ultrasonic waves and which is enclosed by a membrane 17 for being placed into contact with the tissue to be examined. Transducer assembly 16 is described in the reference U.S. Pat. No. 4,484,569 which is incorporated herein by reference.

A pulse echo image and display system 18 is operatively connected to diagnostic transducer 12 for sending and receiving ultrasonic pulses, for example having a center frequency of 10 megahertz. Pulses are radiated into the tissue being examined and the echos of the ultrasonic pulses are received by the pulse-echo and image display system 18 and displayed to an operator. The pulse-echo and image display system 18 is a system which is known and used in the art. The system 10 of FIG. 1 includes a high intensity excitation system 24 and a matching network 26 for providing high intensity ultrasound signals to therapeutic transducer 14. Such signals may typically be at a frequency of 2 megahertz and have a high intensity for providing thermal and mechanical treatment of tissue which is centered around the focal volume of transducer 14.

According to the present invention system 10 includes timing circuits 22 and an analog to digital converter acquisition system 20, for digital radio frequency (RF) echo acquisition from a selected range interval at an externally controlled pulse-repetition frequency using a sampling frequency of 200 MHz. The sampled data may be provided to a computer, for analyzing echo signals received from the tissue in response to the diagnostic ultrasonic signals emitted by transducer 12.

Figure 2A:
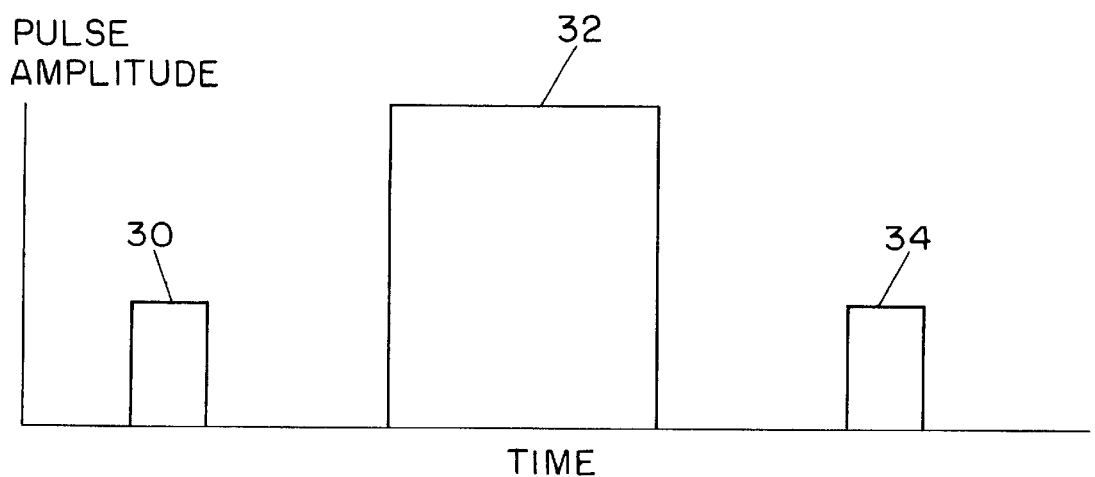
FIGS. 2A and 2B are diagrams showing respective time sequences of ultrasonic therapeutic and diagnostic pulses in accordance with one embodiment of the present invention.
Figure 2B:
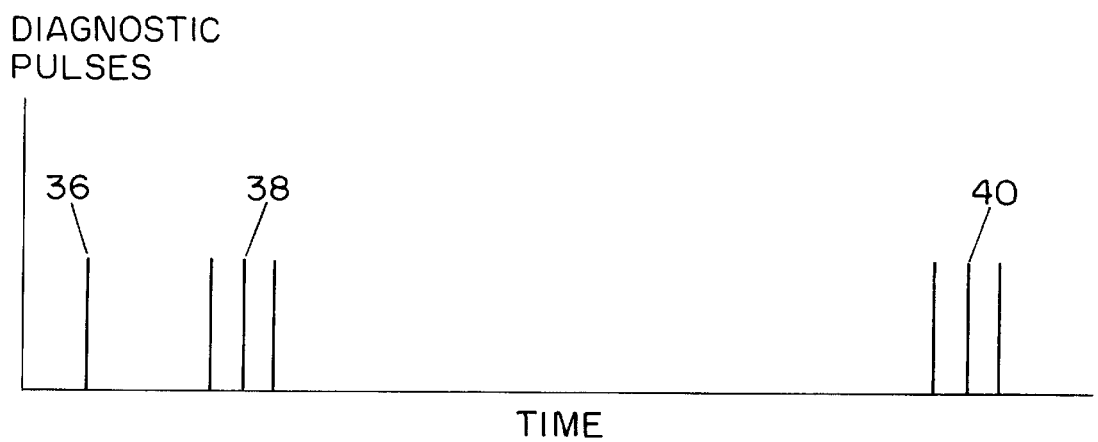

Referring to FIGS. 2A and 2B, there are shown exemplary sequences of respectively high intensity ultrasound radiation from therapeutic transducer 14 and ultrasonic diagnostic pulses from diagnostic transducer 12. The exemplary pulse sequences illustrated represent a first phase of gathering baseline tissue data, a second phase of evaluating elastic tissue characteristics, a treatment phase and a post treatment evaluation of the treated tissue region.

The high intensity pulses depicted in FIG. 2A represent two distinct types of pulses, the first is a stimulus pulse, which is provided to induce tissue motion by radiation force or streaming, so that the tissue displacement and recovery from displacement can be observed using the diagnostic ultrasound system. The second pulse type is a therapy pulse which has higher power and/or a longer time interval to provide a greater amount of energy to the tissue for causing thermal or mechanically induced lesions. Lesions are permanent or long lasting tissue alterations intended to treat disease.

In the sequence shown in FIG. 2, one or a sequence of diagnostic pulses 36 may be used to obtain initial data on tissue structure. Thereafter a stimulus pulse 30 of the high intensity ultrasound is provided during a first time interval, for example 0.2 seconds, and having an instantaneous peak power intensity intended to be sufficiently large to induce internal tissue motion due to radiation force in the exposed tissue. Immediately following the stimulation pulse 30 the diagnostic system is used to acquire several frames of RF echo data which results from diagnostic pulses 38. These pulses immediately follow the stimulus pulse 30 and are intended to track the position and motion of the tissue as it returns to its original condition following stimulus by pulse 30. Echo data from the initial calibration pulse 36 and pulses 38 can be used to record the initial condition of a region of tissue prior to ultrasonic treatment using high intensity excitation system 24 and transducer 14. Once the characteristics of the tissue in its untreated condition are acquired, such as by analog to digital converter and analysis circuits 20, they may be recorded as digital signals in a computer system for analysis and comparison to other signals. For example, in connection with obtaining initial tissue characteristics, the echos received in response to diagnostic pulses 38 may be compared to the echos received in response to diagnostic pulse 36 which is directed into the tissue in an untreated and unstimulated condition. In comparing the pulse echo signals it can be determined how much the tissue has moved in response to the stimulus pulse 30 and how long the tissue takes to return to its initial condition following stimulus 30. Accordingly it is intended that a plurality of pulses 38 will be used to measure the radiation pressure displacement of a region of tissue and also to measure the reaction of the tissue in returning to its initial tissue condition.

The initial diagnostic pulses may also be used for purposes of identifying tissue regions to be treated. For example, tissue areas of interest may have different relaxed state echo characteristics which can be determined by diagnostic pulse 36 for the purpose of identifying a region of tissues to be treated. Diagnostic pulses 38, which follows stimulus 30 can likewise be used to measure the displacement and elastic characteristics of the tissue in connection with identifying a region of tissue to be treated based on its mechanical properties. Prior to use, the diagnostic and therapeutic ultrasound transducer assembly 16 shown in FIG. 1 is aligned so that the approximate focal regions of the diagnostic and therapeutic transducers are aligned in angle and have a common focal region. One or more therapy pulses 32 may then be applied to a tissue region to be treated, and the baseline characteristics of which have been measured and recorded using diagnostic pulses 36 and 38.

The initial diagnostic pulses 36 and 38 can be used with stimulus pulse 30 to determine the position of the focal zone of the therapy transducer; in homogeneous tissue, maximum motion will be detected in this focal zone.

The therapy pulse 32 illustrated in FIG. 2A may be arranged, for example, to provide a focal point intensity of radiation in the range of 500 watts/cm$^2$. This pulse may be provided with a pulse duration of about 1 to about 5 seconds and may be repeated for the same region of tissue or for adjoining regions of tissue to provide energy induced lesions in the tissue. Diagnostic pulse sequences 40 may be used to determine the condition of the tissue immediately after therapy pulse 32 or may be provided after a further stimulus pulse 34 at lower energy and/or shorter duration, is provided to the region of tissue. Diagnostic pulses 40 are intended to further measure the characteristics of the region of tissue after treatment by the therapeutic beam. There may be provided a sequence of therapy pulses 32 prior to measurement by use of stimulus pulse 34 and diagnostic pulses 40. Furthermore, additional diagnostic pulses, similar to 36, may be used preceding each stimulus pulse 34 to establish tissue positions before each stimulus.

Figure 4A:
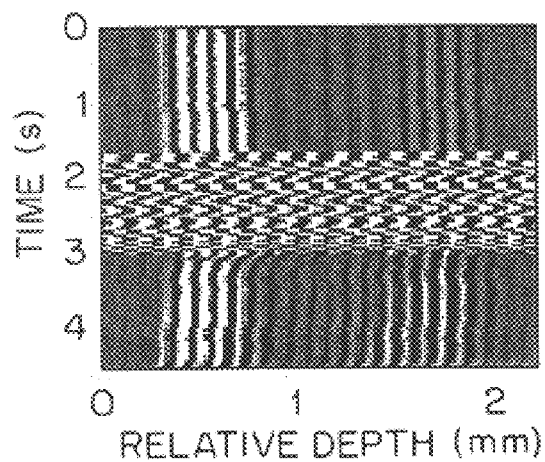
FIG. 4A is a scan echo diagram illustrating tissue motion useful in connection with the practice of the present invention.

FIG. 4A illustrates a continuing sequence of diagnostic pulse echos over a period of 5 seconds on an in vitro sample of liver tissue. During the sequence of diagnostic pulses, there is provided a therapeutic pulse starting at about 1.5 seconds on the time scale and lasting for about 1.1 seconds. Following exposure to the therapeutic ultrasound beam, the diagnostic ultrasound echos are again recorded. In the echo pattern shown in FIG. 4A it can be seen that prior to the therapeutic ultrasound beam, at times of 0 to 1.5 seconds, the tissue being examined is relatively stable and unchanging and includes tissue regions at a depth of about 0.6 mm and 1.8 mm that differ in structure from the remaining tissue in echo characteristics. During exposure to the therapeutic ultrasound, there is noise created by the therapeutic ultrasound beam that renders echo observation noise-like. The echo pattern after the therapeutic radiation shows that the anomalous region of tissue at approximately 0.6 cm depth has been displaced to the right and that the displacement gradually returns to the original pattern. The data also shows that the tissue at 1.8 mm depth had been permanently changed in structural characteristics from the pre-treatment condition. Furthermore, the tissue at 1.8 mm depth shows a lower degree of tissue mobility or elasticity, in that there is only a very small movement of the tissue in recovering from radiation induced displacement of the therapeutic beam.

Figure 4B:
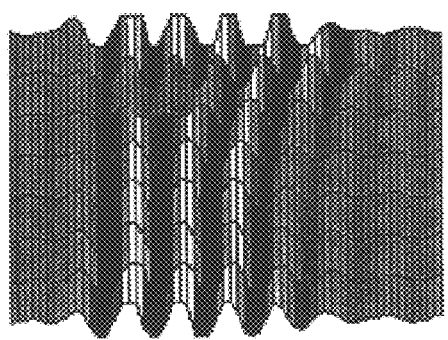
FIG. 4B is a detail of a portion of the echoes of FIG. 4A shown in isometric form.
Figure 4C:
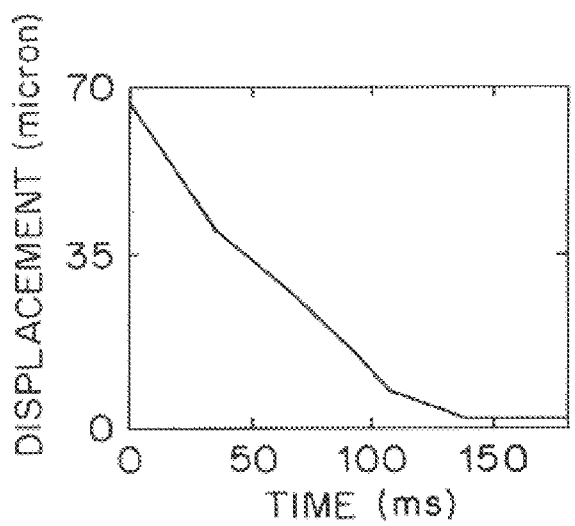
FIG. 4C is a diagram showing tissue displacement as a function of time.

FIG. 4B is an enlarged isometric depiction of diagnostic ultrasound from the tissue region at approximately 0.6 mm depth in the scan results of FIG. 4A. The top signal in FIG. 4B was received immediately before the therapy pulse. The next lower signal was received immediately after the therapy pulse. Subsequently lower traces were received at correspondingly later times, as in FIG. 4A. FIG. 4B shows that the tissue structure has undergone a displacement to the right as a result of radiation pressure caused by the therapeutic beam, and on each subsequent scan the displacement gradually returns to a nominal condition. The displacement of tissue illustrated in FIG. 4B is plotted in FIG. 4C which shows tissue displacement as a function of time in milliseconds following the end of the therapeutic beam. Characteristics of tissue that can be recognized from the plot of FIG. 4C are total tissue displacement, which indicates the tissue stiffness and the ability of the tissue to be moved by radiation pressure, and the time period during which the tissue recovers to its nominal position, which represents the visco-elastic characteristics of the tissue. It has been observed that these characteristics of tissue stiffness and tissue elasticity are changed by creation of therapeutic lesions in the tissue by therapeutic ultrasound beams, and the measurement of ultrasonic echos immediately following use of a higher energy therapeutic or stimulus beam enables the observation of these tissue characteristics.

Using the method of the invention, it is possible to form images of the tissue structure as represented by its mechanical properties properties or to form images of the therapeutic radiation beam. To image structure, such as anomalies in tissue or lesions, the transducer assembly is moved to adjust the tissue location which is stimulated by the high intensity beam and from which echoes are detected. The adjustment can be linear, such as by moving the transducer while maintaining angular orientation or can be angular, such as maintaining transducer location and pivoting the transducer to change the beam direction.

The focal region of the high intensity beam can be mapped by maintaining the high intensity beam at a fixed location and adjusting the relative position of the diagnostic beam, either by linear or angular adjustment.

Analysis of tissue characteristics is most easily performed by comparing the diagnositc ultrasonic echoes taken in the initial tissue condition to the ultrasonic echoes taken immediately after stimulation by the high intensity beam. By capturing the echo data in digital format, the data points can be expanded or contracted in time to achieve correlation between the initial tissue structure and the structure as disturbed by the high intensity beam. The amount of expansion or contraction gives a measure of tissue displacement. Alternatively, a similar analysis can be performed on the Fourier transform of the echo signals using frequency scaling.

Figure 3A:
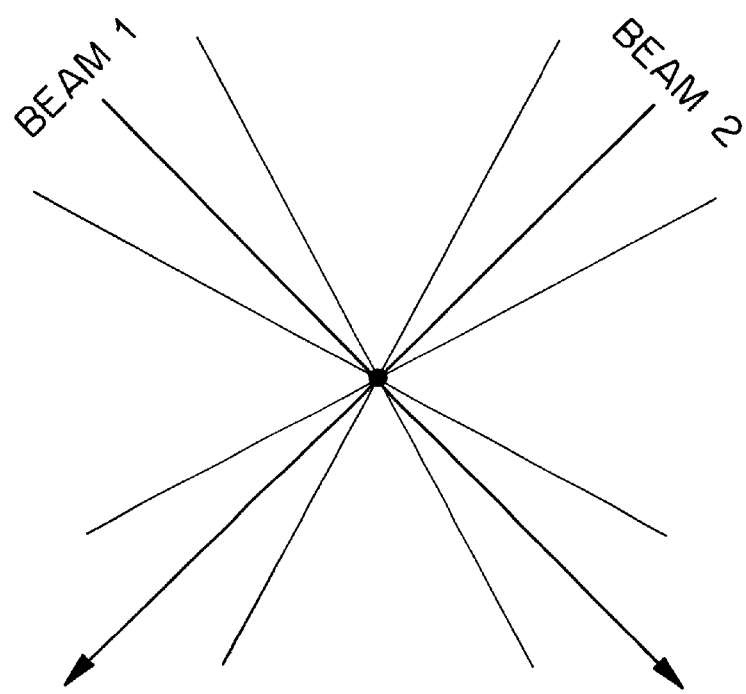
FIGS. 3A and 3B illustrate a method of providing crossing therapeutic ultrasound beams in accordance with another aspect of the present invention.
Figure 3B:
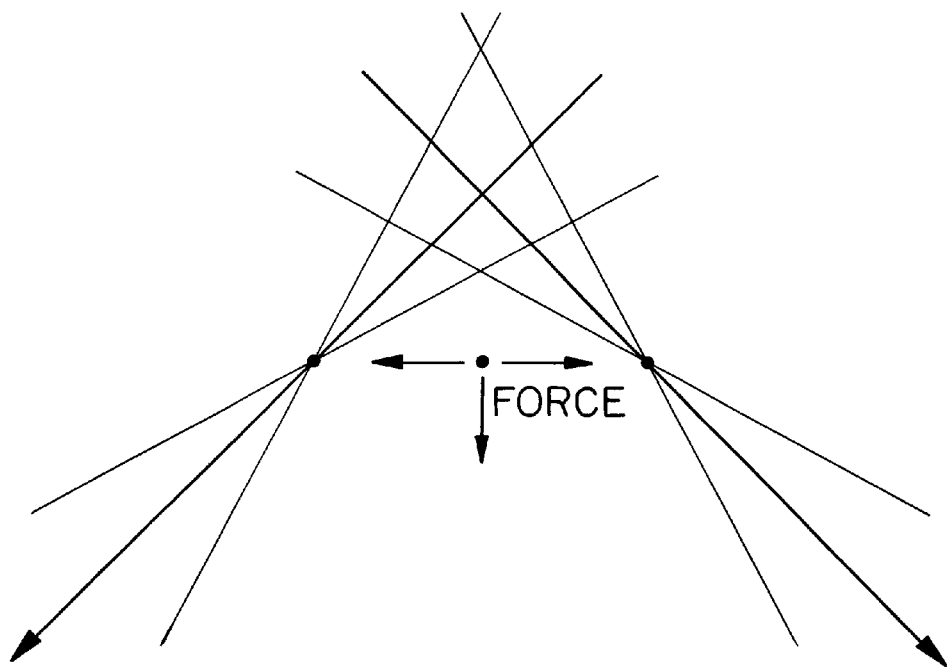

In addition to the arrangement shown in FIG. 1 using a combined diagnostic and ultrasonic transducer, it is possible to apply strains in different directions to tissue for purposes of measuring tissue characteristics. FIG. 3A shows an example of the use of overlapping therapeutic ultrasonic beams with a common focal point for purposes of applying tissue strain. The strain applied in this manner may be measured using a diagnostic ultrasound beam that is directed along one or the other of the therapeutic beams. As shown in FIG. 3B it is also possible to use therapeutic beams having different beam directions in the tissue and having different focal points in order to measure the cross-elasticity and cross-coupling in tissue at a region, for example, between the focal points of the two beams shown in FIG. 3B. The use of two beams as shown in FIG. 3 can produce a lateral motion in tissue. Where the beams have a common focal region as shown in FIG. 3A they can be alternated to produce local agitation which can be monitored with RF echo signals to deduce mechanical properties and monitor the disruption of tissue. Laterally off-set beams as shown in FIG. 3B can produce tensional forces whose induced motions and tissue disruption can also be monitored. Tension is indicated by the oppositely directed horizontal vector components in the force diagram of FIG. 3B.

In multiple beam configurations such as those shown in FIG. 3, induced tissue motion can be sensed using stimulus pulses as in FIG. 2. Multiple diagnostic transducers, colinear with each therapy beam, can be used to track induced motion along the axes of each respective therapy beam. Motion tracking can also be performed using a single pulsed scanned diagnostic beam from a mechanically scanned transducer or from an electronically controlled piezoelectric array. Composite motions, having range and cross-range components, can be tracked by using correlation tracking along selected scan lines, as in FIG. 2, to track motion along scan lines. Motion perpendicular to scan lines can be characterized by cross-scan line correlation procedures.

An additional benefit of observing the dynamics of tissue motion can be realized in selection of pulse repetition frequencies for therapeutic ultrasound which are matched to the time constant of tissue motion. The time constant of tissue motion is determined by observation of the tissue response in returning to normal after an applied strain as shown in FIG. 4C. The time constant is used to select a pulse repetition frequency for therapeutic beams which is matched to the inverse of the time constant. This pulse repetition frequency can then be used with a set of sequential high intensity focused ultrasound therapy pulses to induce tissue motion at its natural frequency and enhance mechanical-lesion phenomena. This would be most used in treating tissue that exhibits mechanical resonances and oscillating motion after the short stimulus high intensity pulses. These procedures could be employed when the subject tissue is vascular where the radiation forces compress blood vessels. This will improve treatment to occlude anomalous blood vessels or to deprive tumors of their blood supply.

The induction and sensing of tissue motion in all described embodiments can be implemented using a single transducer or separate therapeutic and diagnostic arrays capable of generating multiple ultrasonic beams by control of electronic excitation systems. The therapy and diagnostic beams can be scanned along different propagation directions while using the excitation scheme of FIG. 2 to measure initial displacements and recovery times shown in FIG. 4C. The measured displacements and recovery times obtained along an ordered progression of scan lines can then be employed to generate cross-sectional images of the aforesaid parameters. As described for single scan lines, these images would be useful in establishing the location and extent of the therapeutic focal zone in tissue and in imaging induced tissue lesions.

The same monitoring procedures could be used to sense tissue alterations as they are induced by other modalities. In this case, the ultrasonic stimulus pulse 30 and diagnostic pulses 36 and 38 would be used to determine pre-treatment tissue characteristics. The therapy pulse 32 would be replaced by a dose delivered by an alternative therapy modality such as intense lasers, RF electromagnetic ablation energy, microwave energy, or alcohol injection to destroy tissue. Induced tissue changes would be monitored by subsequent repetition of pulses 36, 32 and 38 to sense induced transient or permanent changes in tissue mechanical characteristics.

While there have been what are believed to be the preferred embodiment of the invention, those skilled in the art will recognize that other and further changes may be made thereto without departing from the spirit of the invention and it is intended to claim all such changes and modifications as fall within the true scope of the invention.

We claim:

1. A method for treating and evaluating tissue characteristics, comprising:
   providing an ultrasonic therapeutic transducer for insonifying a region of tissue;
   operating said ultrasonic therapeutic transducer to treat a region of tissue
   providing an ultrasonic diagnostic transducer for transmitting and receiving signals from a region of tissue;
   operating said ultrasonic therapeutic transducer to insonify a selected region of tissue and cause induced tissue displacement; and
   operating said ultrasonic diagnostic transducer to observe said induced tissue displacement and thereby to evaluate mechanical characteristics of said tissue.

2. A method as specified in claim 1 wherein said therapeutic transducer illuminates said tissue along a radiation axis and wherein said diagnostic transducer transmits and receives ultrasonic signals along said radiation axis.

3. A method as specified in claim 1 wherein said operating an ultrasonic therapeutic transducer to induce tissue displacement comprises operating said transducer during a first selected time interval, and wherein said operating an ultrasonic diagnostic transducer comprise operating said diagnostic transducer during a second selected time interval immediately following said first selected time interval.

4. A method as specified in claim 1 further comprising observing baseline mechanical properties of said tissue prior to treating said region of tissue by irradiating said tissue with a reduced energy pulse of said therapeutic ultrasound radiation during a first selected time interval and observing mechanical characteristics of said tissue region during a second selected time interval immediately following said first time interval using said diagnostic ultrasound to thereby observe baseline mechanical characteristics of said tissue region.

5. A method as specified in claim 1 wherein said step of observing induced motion of said tissue region comprises irradiating said tissue region with a reduced energy pulse of said therapeutic ultrasound radiation during a first selected time interval and observing induced motion of said tissue region during a second selected time interval immediately following said first time interval using said diagnostic ultrasound.

6. A method as specified in claim 1 further comprising evaluating effectiveness of said treating said region of tissue from said evaluation of mechanical characteristics of said tissue.

7. A method as specified in claim 1 further comprising locating the focal volume of said therapeutic transducer by observing said induced tissue displacement using said ultrasonic diagnostic transducer.

8. A method as specified in claim 7 wherein said step of locating the focal volume of said therapeutic ultrasound radiation comprises irradiating said tissue region with a reduced energy pulse of said therapeutic ultrasound radiation during a first selected time interval and observing mechanical characteristics of said tissue region during a second selected time interval immediately following said first selected time interval using said diagnostic ultrasound to thereby locate the focal volume of said therapeutic radiation in said tissue.

9. A method of locating the focal volume of an ultrasonic therapeutic transducer in tissue, comprising:
   detecting ultrasonic echoes from said tissue to determine initial structure thereof;
   stimulating said tissue using ultrasonic radiation from said therapeutic transducer during a first selected time interval to induce tissue displacement; and
   detecting diagnostic ultrasonic echoes from said tissue during a second time interval immediately following said first time interval thereby to detect a region of said tissue corresponding to the focal volume of said therapeutic transducer.

10. A method for treating tissue using high intensity ultrasound radiation comprising:
    stimulating said tissue with high intensity ultrasonic radiation from an ultrasonic therapeutic transducer during a first selected time period;
    detecting diagnostic ultrasonic echoes from said tissue using an ultrasonic diagnostic transducer during a second time interval immediately following said first time interval thereby to determine mechanical properties of said tissue; and
    exposing said tissue to therapeutic high intensity ultrasonic pulses in a pulse sequence selected according to said mechanical properties.

11. A method as specified in claim 10 wherein determining mechanical properties includes determining elastic properties and wherein said pulse sequence is selected to have a pulse frequency corresponding to said elastic properties.

12. A method for measuring mechanical properties of tissue comprising:
    stimulating a region of tissue with first and second high intensity ultrasonic radiation beams having first and second radiation axes; and
    detecting diagnostic ultrasonic echoes from said region of tissues during a time interval immediately following said stimulating thereby to determine mechanical properties of said tissue.

13. A method as specified in claim 12 wherein said first and second high intensity beams are in sequential pulses and wherein said diagnostic echoes are detected during time intervals between said first and second sequential pulses.

14. A method of forming an image representing characteristics of a region of tissue, comprising:

stimulating said tissue with high intensity ultrasonic radiation from an ultrasonic therapeutic transducer during a first selected time interval to induce tissue displacement;

detecting ultrasonic echoes from said tissue using a diagnostic ultrasonic transducer during a second time selected time interval immediately following said first time interval thereby to measure mechanical characteristics of said tissue;

adjusting the tissue location of said diagnostic ultrasonic transducer and repeating said detecting to measure mechanical properties of said tissue over a plurality of tissue locations; and combining said measurements to form an image of said tissue.

15. A method as specified in claim 14 wherein said adjusting the tissue location comprises maintaining a constant location of said high intensity ultrasonic radiation and adjusting the tissue location of said diagnostic ultrasonic echoes thereby to form a tissue image mapping a focal volume of said high-intensity radiation in said tissue.

16. A method as specified in claim 14 wherein said tissue includes a lesion and wherein said tissue image represents the location of said lesion.

17. A method as specified in claim 14 wherein said repeating said detecting includes repeating said stimulating.

18. A method for applying stress to tissue comprising insonifying said tissue with first and second therapeutic ultrasound beams having a common focal point in said tissue and having different beam directions toward said common focal point.

19. A method for applying stress to tissue as specified in claim 18 wherein said first and second beams are alternated.

20. A method for measuring tissue characteristics comprising applying stress to said tissue using the method of claim 18 and detecting diagnostic ultrasonic echoes from said tissue using an ultrasonic diagnostic transducer to monitor tissue motion resulting from said applied stress.

21. A method for applying stress to tissue comprising insonifying said tissue with first and second therapeutic ultrasound beams having a focal points spaced from each other in said tissue and having different beam directions toward said focal points.

22. A method for applying stress to tissue as specified in claim 21 wherein said first and second beams are alternated.

23. A method for measuring tissue characteristics comprising applying stress to said tissue using the method of claim 21 and detecting diagnostic ultrasonic echoes from said tissue using an ultrasonic diagnostic transducer to monitor tissue motion resulting from said applied stress.

* * * * *

UNITED STATES PATENT AND TRADEMARK OFFICE
CERTIFICATE OF CORRECTION

PATENT NO.    : 6,488,626 B1
DATED         : December 3, 2002
INVENTOR(S)   : Lizzi et al.

It is certified that error appears in the above-identified patent and that said Letters Patent is hereby corrected as shown below:

Title page,
Item [56], References Cited, OTHER PUBLICATIONS, "Nightingale," "et al" should read -- et al., --

Column 1,
Line 18, "echos" should read -- echoes --

Column 3,
Line 19, "echos" should read -- echoes --

Column 4,
Lines 13, 14 and 66, "echos" should read -- echoes --
Line 30, "follows" should read -- follow --

Column 5,
Lines 5 and 45, "echos" should read -- echoes --
Line 41, "visco-elastic" should read -- viscoelastic --
Line 50, "properties" (second occurrence) should be deleted
Line 65, "diagnositc" should read -- diagnostic --

Column 6,
Line 34, "colinear" should read -- collinear --

Column 7,
Line 37, "tissue" should read -- tissue; --
Line 55, "comprise" should read -- comprises --

UNITED STATES PATENT AND TRADEMARK OFFICE
CERTIFICATE OF CORRECTION

PATENT NO. : 6,488,626 B1
DATED : December 3, 2002
INVENTOR(S) : Lizzi et al.

It is certified that error appears in the above-identified patent and that said Letters Patent is hereby corrected as shown below:

Column 9,
Line 10, "time" should be deleted
Line 12, "time interval" should read -- selected time interval --
Lines 5 and 23, "high intensity" should read -- high-intensity --

Column 10,
Line 17, "a" should be deleted

Signed and Sealed this

Twenty-ninth Day of July, 2003

JAMES E. ROGAN
*Director of the United States Patent and Trademark Office*